United States Patent [19]

Van Hoogstraten

[11] 4,092,149

[45] May 30, 1978

[54] METHOD OF INCREASING THE YIELD OF COTTON PLANTS

[75] Inventor: Samuel David Van Hoogstraten, Cambridge, England

[73] Assignee: Fisons Limited, London, England

[21] Appl. No.: 795,552

[22] Filed: May 10, 1977

[30] Foreign Application Priority Data

May 15, 1976 United Kingdom ............... 20146/76

[51] Int. Cl.² .............................................. A01N 9/12
[52] U.S. Cl. ............................................ 71/90; 71/76
[58] Field of Search ....................................... 71/90, 76

[56] References Cited

U.S. PATENT DOCUMENTS 3,770,754  11/1973  Parsons ................................ 71/90 X
4,035,175  7/1977  Brouwer et al. ......................... 71/76

*Primary Examiner*—Catherine L. Mills
*Attorney, Agent, or Firm*—Wenderoth, Lind & Ponack

[57] ABSTRACT

There is provided a method of increasing the branching, boll set or yield of cotton plants in which (3-phenyl-1,2,4-thiadiazol-5-ylthio)acetic acid or a salt, ester or amide thereof is applied in an effective amount to the locus at which the plants are growing.

10 Claims, No Drawings

METHOD OF INCREASING THE YIELD OF COTTON PLANTS

This invention concerns a method of plant growth regulation.

(3-Phenyl-1,2,4-thiadiazol-5-ylthio)acetic acid is a known compound, but hitherto its suprisingly good plant growth regulant activity with respect to cotton has not been appreciated.

In one aspect, therefore, this invention provides a method of regulating the growth of cotton plants, in which (3-phenyl-1,2,4-thiadiazol-5-ylthio)acetic acid or a non-phytotoxic functional derivative thereof is applied to the locus at which the plants are growing, in an amount sufficient to exert its plant growth regulant effect.

For convenience of use, salts, especially water-soluble salts of (3-phenyl-1,2,4-thiadiazol-5-ylthio)acetic acid are preferred, e.g. alkali-metal salts or salts with amines, and especially the sodium, triethylamine, tributylamine, diethanolamine and triethanolamine salts. Alternatively, the free acid, or esters (especially those formed with alkanols of 1 to 10 carbon atoms, for example the isobutyl, heptyl, 1-methylheptyl and nonyl esters), or the amide thereof may be employed.

The active compound may be applied to the crop in a single application, or in two or more discrete applications. The total rate applied is preferably from ⅛ oz to 4 lbs per acre, rates of 1 oz to 1 lb/acre, being most preferred.

For application, the active compound is preferably formulated into an appropriate composition with a suitable carrier and/or wetting agent. Thus, the compound may, for example, be formulated into a solution or suspension in an appropriate liquid medium, or into a wettable powder by admixture with a wetting agent and, if desired, an inert diluent. Suitable liquid media include water (in which case the compositions preferably also contain a wetting agent) and water-immiscible solvents, for example high boiling hydrocarbons, suitably containing dissolved emulsifying agents so that the composition acts as a self-emulsifiable oil on addition to water. The liquid may be a water-miscible solvent, e.g 2-methoxyethanol, methanol, propylene glycol, diethylene glycol, diethylene glycol monoethyl ether, formamide or methylformamide.

Inert diluents with which the compound may be admixed to form a powder include powdered or finely-divided solid materials such as clays, sands, talc, mica, peat, fertilizers and soil. If desired, the compound may be used to impregnate or coat preformed granules of, for example, peat or limestone.

Wettable powders soluble or dispersible in water may be formed by admixing the compound in particulate form with a paticulate carrier or spraying molten compound on to the particulate carrier, admixing a wetting agent and a dispersing agent and finely grinding the whole powder mixture.

An aerosol composition may be formed by admixing the compound with a propellant e.g a polyhalogenated alkane such as dichlorodifluoromethane, and suitably also with a solvent.

A flowable suspension concentrate may be formed by grinding the compound with water, a wetting agent and a suspending agent.

The wetting agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The wetting agents may also comprise non-ionic agents, for example condensation products of fatty acid esters, fatty alcohols, fatty acid amides or alkyl-substituted phenols with ethylene oxide, fatty esters of polyhydric alcohol esters e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7diol, or ethoxylated acetylenic glycols.

The wetting agents may also comprise cationic agents, for example alkyl- and/or aryl-substituted quarternary ammonium compounds such as cetyl trimethyl-ammonium bromide, or ethoxylated tertiary fatty amines.

Preferred wetting agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The compositions which are employed may contain other active materials in addition to the plant growth regulants defined hereinbefore, for example other plant growth regulants, such as 2,3,5-triiodobenzoic acid, (2-chloroethyl)phosphonic acid, (2-chloroethyl)-trimethylammonium chloride, maleic hydrazide, N,N-dimethylaminosuccinamic acid, 1-carboxyethyl-3-chlorocarbanilate or N-1-naphthylphthalamic acid, or morphactins, for example 2-chloro-9-hydroxyfluorene-9-carboxylic acid (methyl ester) or 9-hydroxyfluorene-9-carboxylic acid (butyl ester), pesticides, such as dichloro-diphenyl-trichloroethane, carbaryl or dimethoate; herbicides, for example 2,4-dichlorophenoxy-acetic acid, 2-methyl-4-chlorophenoxyacetic acid, or substituted triazines or ureas, e.g 2chloro-4,6-bis(ethylamino)-s-triazine; or fungicides, such as copper compounds or dithiocarbamates. If a further active material is employed, it is preferably in a ratio by weight of from 1:4 to 4:1 to the plant growth regulants defined hereinbefore.

The compositions which are employed are conveniently produced initially as concentrates for dilution before application. Such concentrates conveniently contain from 0.5 to 80% by weight, for example from 10 to 50% by weight of the plant growth regulants defined hereinbefore.

The compositions may be applied by any method appropriate to the particular formulation employed, for example spraying. The concentration of wetting agent in the formulation applied is preferably from 100 to 4,000 parts per million, more preferably from 500 to 2,000 parts per million.

The plant growth regulant effect observed is generally increased yield of cotton accompanied by or occasioned by increased branching and boll set. Thus, if the active compound is applied at the vegetative stage, i.e before flowering, for example at about the 6 fully expanded leaves stage, the main effects observed are increased branching and yield, whereas, if applied during flowering, e.g at first flower, or when in full bloom, the main effects are increased boll set and yield. A further effect may also be observed, namely earlier opening of the bolls.

Application of the active compound may be made both during the vegetative stage and during flowering. The ratio of the rates applied at the two stages is desirably in the range 1:10 to 100:1, especially from 1:1 to 4:1, e.g from 0.1 to 3.0 lb/acre at the vegetative stage, especially from 0.25 to 1.0 lb/acre, and from 0.03 to 1.0 lb/acre, especially from 0.1 to 0.5 lb/acre, during flowering.

The invention is further described, though only by way of illustration, in the following Examples.

EXAMPLE 1

(3-Phenyl-1,2,4-thiadiazol-5-ylthio)acetic acid triethanolamine salt was applied in aqueous solution as set out in the table below at first flower at 1 lb/acre to Stoneville 213 cotton plants cultured individually in a greenhouse in 5-gallon polyvinylchloride containers filled with Bosket sandy loam. In each application 12 gallons spray volume per acre were applied. The cotton plants were planted in February and flowered during April and early May. The results obtained were as follows:

| When applied | Application rate | Total Per Plant | | |
|---|---|---|---|---|
| | | flowers | bolls | seed cotton (g) |
| At first flower | 1 lb/acre | 30 | 16 | 64 |
| At first flower | 0 (Control) | 27 | 14 | 58 |

From the above, it can be seen that the number of flowers and bolls, and the total yield of seed cotton are increased relative to control.

EXAMPLE 2

(3-Phenyl-1,2,4thiadiazol-5-ylthio)acetic acid triethanolamine salt was applied in aqueous solution at rates of 0.128 and 0.512 lb/acre to SJ2 Acala cotton plants grown about 6 inches apart in 30 inch spaced rows (about 26,000 plants per acre). Three replications were performed at each rate. The plants were sprayed at the early flowering stage with a spray volume of 56 lb/acre.

The treatments induced additional branching, and as set out below, yield increases and earlier opening of the bolls relative to an untreated control.

| lb/acre | Yield lb/acre | % of bolls open at first picking |
|---|---|---|
| 0.128 | 1648 | 88.3 |
| 0.512 | 1530 | 84.1 |
| 0 (Control) | 1380 | 83.9 |

EXAMPLE 3

(3Phenyl-1,2,4-thiadiazol-5-ylthio)acetic acid triethanolamine salt was applied in aqueous solution at rates set out below, together with 37.5 ml of wetting agent X-77 (alkylarylpolyoxyethylene glycols, free fatty acids and isopropanol mixture by Colloidal Products Corporation) per 100 US gallons of formulation applied, to Coker 210 cotton plants grown in 40 inch spaced rows and a density of about 50,000 plants per acre. The plants were sprayed at various times T1 (6 leaf stage), T2 (early flowering) and T3 (full flowering) and at various rates as set out below, there being four replications for each treatment. The spray volume applied was 40 US gal/acre.

| Treatment No. | Time | Rate (ai) (lb/acre) | Yield (lb/acre) |
|---|---|---|---|
| 1 | — | 0 (Control) | 2020 |
| 2 | T1 | 0.25 | 2363 |
| 3 | T1 | 0.5 | 2297 |
| 4 | T1 | 1.0 | 2350 |
| 5 | T2 | 0.25 | 2125 |
| 6 | T2 | 0.5 | 2297 |
| 7 | T2 | 1.0 | 2455 |
| 8 | T3 | 0.125 | 2244 |
| 9 | T3 | 0.25 | 2336 |
| 10 | T3 | 0.5 | 2072 |
| 11 | T1 + T3 | 0.5 + 0.25 | 2244 |
| 12 | T1 + T3 | 0.5 + 0.5 | 2415 |
| 13 | T1 + T3 | 0.25 + 0.25 | 2521 |

EXAMPLE 4

(3-Phenyl-1,2,4-thiadiazol-5-ylthio)acetic acid triethanolamine salt was applied in aqueous solution at rates set out below to Coker 210 cotton plants grown in 40 inch spaced rows and a density of about 50000 plants per acre. The plants were treated at times T1, T2, and T3 as defined in Example 3. In addition, a nitrogen fertilizer was applied foliarly at mid-flowering at a rate of 20 lb/acre nitrogen. The control was treated also with the fertilizer. Results obtained, there being four replications at each rate, were as follows:

| Treatment No. | Time | Rate (ai) (lb/acre) | Yield (lb/acre) |
|---|---|---|---|
| 1 | Untreated | (Control) | 2297 |
| 2 | T1 | 0.25 | 2363 |
| 3 | T1 | 0.5 | 2323 |
| 4 | T1 | 1.0 | 2311 |
| 5 | T2 | 0.25 | 2469 |
| 6 | T2 | 0.5 | 2429 |
| 7 | T2 | 1.0 | 2534 |
| 8 | T3 | 0.125 | 2468 |
| 9 | T3 | 0.25 | 2297 |
| 10 | T3 | 0.5 | 2574 |
| 11 | T1 + T3 | 0.5 + 0.25 | 2429 |
| 12 | T1 + T3 | 0.5 + 0.5 | 2363 |
| 13 | T1 + T3 | 0.25 + 0.25 | 2403 |

I claim:
1. A method of increasing the yield of cotton plants, in which (3-phenyl-1,2,4-thiadiazol-5-ylthio)acetic acid, or a salt, an ester formed with an alkanol of 1 to 10 carbon atoms, or the amide thereof is applied in an effective amount to the locus at which the plants are growing.

2. A method according to claim 1 wherein a salt is employed which is a water-soluble salt.

3. A method according to claim 2 wherein the water-soluble salt is selected from the group consisting of alkali-metal and amine salts.

4. A method according to claim 1 wherein a salt is employed which is selected from the group consisting of the sodium, triethylamine, tributylamine, diethanolamine, and triethanolamine salts.

5. A method according to claim 1 wherein the active ingredient is applied to the locus in an amount in total of from ⅛ oz to 4 lb per acre.

6. A method according to claim 5 wherein the total amount applied is from 1 oz to 1 lb per acre.

7. A method according to claim 1 wherein the active ingredient is applied to the locus in at least two discrete applications.

8. A method according to claim 7 wherein the active ingredient is applied to the locus both before and after flowering of the crop.

9. A method according to claim 8 wherein the ratio of the amount of active ingredient applied before flowering to the amount of active ingredient applied after flowering lies in the range 1:1 to 4:1.

10. A method according to claim 1 wherein the active ingredient is applied in a composition comprising a suitable carrier and from 100 to 4000 parts per million of a wetting agent.

* * * * *